United States Patent
Harada et al.

(10) Patent No.: US 9,556,212 B2
(45) Date of Patent: Jan. 31, 2017

(54) CHEMICAL DEPOSITION RAW MATERIAL FORMED OF RUTHENIUM COMPLEX AND METHOD FOR PRODUCING THE SAME, AND CHEMICAL DEPOSITION METHOD

(71) Applicant: Tanaka Kikinzoku Kogyo K.K., Chiyoda-ku (JP)

(72) Inventors: Ryosuke Harada, Tsukuba (JP); Naoki Nakata, Tsukuba (JP); Masayuki Saito, Tsukuba (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 129 days.

(21) Appl. No.: 14/422,292

(22) PCT Filed: Aug. 19, 2013

(86) PCT No.: PCT/JP2013/072080
§ 371 (c)(1),
(2) Date: Feb. 18, 2015

(87) PCT Pub. No.: WO2014/030609
PCT Pub. Date: Feb. 27, 2014

(65) Prior Publication Data
US 2015/0225437 A1     Aug. 13, 2015

(30) Foreign Application Priority Data

Aug. 20, 2012  (JP) ................................. 2012-181329

(51) Int. Cl.
C07F 15/00   (2006.01)
C23C 16/18   (2006.01)
C23C 16/46   (2006.01)

(52) U.S. Cl.
CPC .......... *C07F 15/0046* (2013.01); *C23C 16/18* (2013.01); *C23C 16/46* (2013.01)

(58) Field of Classification Search
CPC ....... C07F 15/0046; C23C 16/18; C23C 16/46
USPC .......................................... 556/136; 427/252
See application file for complete search history.

(56) References Cited

U.S. PATENT DOCUMENTS 6,063,705 A   5/2000  Vaartstra
8,753,718 B2  6/2014  Dussarrat et al.
2010/0221577 A1  9/2010  Dussarrat

FOREIGN PATENT DOCUMENTS

| JP | 2002523634 A | 7/2002 |
| JP | 2006057112 A | 3/2006 |
| JP | 2010504424 A | * 9/2006 |
| JP | 2010504424 A | 2/2010 |
| JP | 2010173979 A | 8/2010 |
| WO | WO 2004050947 A | 6/2004 |

OTHER PUBLICATIONS

Deposition of Conductive Ru and RuO$_2$ Thin Films Employing a Pyrazolate Complex [Ru(CO)$_3$(3,5-(CF$_3$)$_2$-pz]$_2$ as the CVD Source Reagent, Yi-Hwa Song et al., Chemical Vapor Deposition 2003, 9, No. 3, 2003 WILEY-VCH Verlag GmbH: & Co. KGaA, Weinheim, pp. 162-169.
Chemical Vapor Deposition of Ruthenium and Osmium Thin Films Using (Hexafluoro-2-butyne)tetracarbonylruthenium and -osmium, Yoshide Senzaki et al, Department of Chemistry, University of Minnesota, Minneapolis, Minnesota 55455; and 3M Corporation Research Laboratories, St. Paul, Minnesota 55144; Chem. Mater. 1993, 5, 1993 American Chemical Society, pp. 1715-1721.
International Search Report for PCT/JP2013/072080 dated Nov. 12, 2013.

* cited by examiner

*Primary Examiner* — Porfirio Nazario Gonzalez
(74) *Attorney, Agent, or Firm* — Orrick Herrington & Sutcliffe, LLP

(57) ABSTRACT

The present invention provides a raw material, formed of a ruthenium complex, for producing a ruthenium thin film or a ruthenium compound thin film by a chemical deposition method, wherein the ruthenium complex is a ruthenium complex represented by the following formula, in which carbonyl groups and a fluoroalkyl derivative of a polyene are coordinated to ruthenium. The present invention provides a raw material for chemical deposition having a preferable decomposition temperature, and the production cost therefor is low:

$(nR\text{-}L)Ru(CO)_3$        [Chemical Formula 1]

wherein L is a polyene having a carbon number of from 4 to 8 and 2 to 4 double bonds, wherein the polyene L has n (n≥1) pieces of substituents Rs, wherein the substituents Rs are each a fluoroalkyl group having a carbon number of from 1 to 6 and a fluorine number of from 1 to 13, and in the case when the polyene L has two or more (n≥2) of the substituents Rs, the carbon numbers and the fluorine numbers of the substituents Rs may be different in the same molecule.

14 Claims, 3 Drawing Sheets

PICTURE OF UPPER PART OF SUBSTRATE

PICTURE OF LOWER PART OF SUBSTRATE

CHEMICAL DEPOSITION RAW MATERIAL FORMED OF RUTHENIUM COMPLEX AND METHOD FOR PRODUCING THE SAME, AND CHEMICAL DEPOSITION METHOD

TECHNICAL FIELD

The present invention relates to a raw material for producing a ruthenium thin film or a ruthenium compound thin film by a chemical deposition method. Specifically, the present invention relates to a raw material for chemical deposition formed of a ruthenium complex, which has suitable stability and a high vapor pressure.

BACKGROUND ART

As ruthenium complexes that constitute raw materials for forming ruthenium thin films by chemical deposition methods such as a CVD process and an ALD process, various ruthenium complexes have been known heretofore. As the ruthenium complexes that have been reported to be useful among those, the following ruthenium complexes are exemplified.

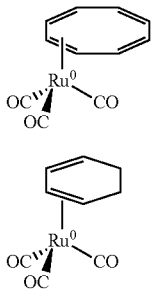

[Chemical Formula 1]

[Chemical Formula 2]

The above-mentioned two ruthenium complexes are such that carbonyl groups and a polyene having plural double bonds (cyclooctatetraene, cyclohexadiene) are coordinated as ligands for ruthenium. The reasons why these ruthenium complexes are useful as raw materials for chemical deposition method include, firstly, that they have high vapor pressures. A compound having a high vapor pressure can feed a raw material gas at a high concentration, and thus can improve film formation efficiency. Furthermore, these ruthenium complexes also have an advantage that the decomposition temperatures are relatively low. The advantage allows the film formation temperature to be set to a low temperature, and stable formation of a thin film while suppressing the damage of a substrate is enabled.

RELATED ART DOCUMENTS

Patent Documents

Patent Document 1: JP 2010-173979 A
Patent Document 2: JP 2006-57112 A

SUMMARY OF THE INVENTION

Problems to be Solved by the Invention

However, according to the present inventors, the above-mentioned ruthenium complexes have the following points that require improvement. Firstly, either of the above-mentioned ruthenium complexes has an advantage that the decomposition temperature is low, but the temperature tends to be slightly too low. In the formation of a thin film by a chemical deposition method, a raw material container is heated to thereby vaporize a raw material compound, and the raw material gas is then introduced into a film formation chamber, but if the decomposition temperature is too low, decomposition of the raw material compound occurs at the stage of the heating vaporization. This leads to the lowering of the utility rate of the raw material compound.

The second problem of the above-mentioned ruthenium complexes is the production costs thereof. The method for synthesizing the above-mentioned ruthenium complexes is generally by reacting a carbonyl compound of ruthenium and a polyene, but this synthesis reaction does not progress unless the polyene is used in a considerably excess amount. For example, in the ruthenium complex of Chemical Formula 1, dodecacarbonyltriruthenium (DCR) and cyclooctatetraene (derivative) are reacted, and 6 to 7-fold equivalent amount of DCR with respect to the cyclooctatetraene is required. Therefore, excess use of the polyene increased the production cost of the ruthenium complex. Furthermore, with respect to the ruthenium complex of Chemical Formula 1, the synthesis reaction of this complex is basically a photoreaction, and thus irradiation of light is required during the synthesis, and this is also a cause for the increase of the cost for the synthesis.

It is difficult to say that the above-mentioned disadvantages of the ruthenium complexes of Chemical Formulas 1 and 2 are fatal for the formation of thin films. However, in order to utilize chemical deposition methods for the formation of respective electrodes for which further miniaturization or complication or multi-layerization will be intended in the future, it is necessary to apply a ruthenium complex having a suitable decomposition temperature (stability). Furthermore, in order to suppress the cost increase for various devices, the costs for the synthesis of those ruthenium complexes are required to be lower. In addition, the development of a ruthenium complex that responds to these requirements and also has conventionally-required properties (high vapor pressure and low melting point) is desired. The present invention has been made against the above-mentioned background, and aims at providing a raw material for chemical deposition formed of a ruthenium complex, which has a suitable decomposition temperature, a high vapor pressure and such a melting point that the raw material liquefies at an ordinary temperature, and requires low production costs.

Means for Solving the Problems

The present invention, which solves the above-described problem, is a raw material for producing a ruthenium thin film or a ruthenium compound thin film by a chemical deposition method, which is formed of a ruthenium complex, wherein the ruthenium complex is a ruthenium complex represented by the following formula, in which carbonyl groups and a fluoroalkyl derivative of a polyene are coordinated to ruthenium:

(nR-L)Ru(CO)$_3$              [Chemical Formula 3]

wherein L is a polyene having a carbon number of from 4 to 8 and 2 to 4 double bonds, wherein the polyene L has n (n≥1) pieces of substituents R, wherein the substituents Rs are each a fluoroalkyl group having a carbon number of from 1 to 6 and a fluorine number of from 1 to 13, and in the case when the polyene L has two or more (n≥2) of the substituents Rs, the carbon numbers and the fluorine numbers of the substituents Rs may be different in the same molecule.

The ruthenium complex that constitutes the raw material for chemical deposition according to the present invention is a ruthenium complex to which three carbonyl groups and a polyene in which fluoroalkyl group(s) has/have been introduced as substituent(s) are coordinated as ligands for ruthenium. Specifically, in contrast to the above-mentioned conventional ruthenium complexes, it is a ruthenium complex in which the polyene as a ligand is partially substituted with the fluoroalkyl group(s).

The reason why the fluoroalkyl group(s) is/are introduced in the polyene in the present invention is that the stability of the ruthenium complex is improved to adjust the decomposition temperature thereof to be within a suitable range. This is due to that the bonding between the Ru and polyene is strengthened by introducing fluoroalkyl groups ($CF_3^-$, $C_2F_5^-$ and the like), which are electron withdrawing groups, into the polyene, and thus the stability of the ruthenium complex molecule is increased, and the decomposition at low temperatures is suppressed.

Furthermore, the improvement of the stability by the introduction of the fluoroalkyl group(s) allows easy progress of the reaction for synthesizing the ruthenium complex (the bonding of the ruthenium and polyene). This can significantly reduce the use amount of the polyene in reacting the ruthenium compound and the polyene. Furthermore, this reaction can be progressed by a thermal reaction, and time and effort as in photoreactions are unnecessary. The method for producing the ruthenium complex in the present invention will be mentioned below.

Furthermore, the significance of introducing the fluoroalkyl group(s) as the substituent(s) is that there is an advantage that the vapor pressure is increased more than the cases when other substituent(s) such as alkyl groups including a methyl group and the like is/are introduced. The reason therefor is considered that the Van der Waals force between the molecules is decreased by introducing the fluoroalkyl group(s). By using the ruthenium complex that has a high vapor pressure, a raw material gas with a high concentration can be generated, and thus efficient formation of a thin film is enabled.

Furthermore, the introduction of the substituent(s) into the polyene also has an effect of lowering the melting point of the ruthenium complex to a low temperature, and the introduction of the fluoroalkyl group(s) also exerts this effect. The effect of the lowering of the melting point by the introduction of the substituent(s) increases in accordance with the increase of the molecular weight(s) of the substituent(s). Furthermore, by this way, the ruthenium complex can be in a liquid state even in an ordinary temperature range, and thus the efficiency of the vaporization of the raw material becomes fine in the production of a thin film.

With respect to the constitution of the ruthenium complex that constitutes the raw material for chemical deposition according to the present invention having the above-mentioned advantages, the polyene has a carbon number of from 4 to 8, and has 2 to 4 double bonds. The reason why the carbon number and double bonds are within these ranges is that, if the molecular weight of the polyene is too high, the melting point increases, and thus the polyene becomes solid at room temperature. The polyene includes both a chain polyene and a cyclic polyene. A preferable chain polyene or cyclic polyene has a carbon number of from 4 to 6, and has two double bonds. The reason why the carbon number and double bonds are within such ranges is that a high vapor pressure and suitable stability can be obtained.

Furthermore, the fluoroalkyl groups that are introduced as the substituents in the polyene each has a carbon number of from 1 to 6 and a fluorine number of from 1 to 13. The reason for these ranges is that the vapor pressure is lowered if the carbon number of the fluoroalkyl group becomes too many. Furthermore, a fluoroalkyl group having a carbon number of from 1 to 3 and a fluorine number of from 1 to 7 is preferable. The number (n) of the fluoroalkyl group(s) may be any number as long as one or more group is introduced. Furthermore, in the case when plural fluoroalkyl groups are introduced into the polyene (in the case when n≥2), different fluoroalkyl groups may be introduced, and the carbon numbers and fluorine numbers thereof may be different in the same molecule. A preferable number of the fluoroalkyl group(s) is 1 to 2.

Specific examples of the ruthenium complex in the present invention having the above-mentioned effect include ruthenium complexes having the following structural formulas.

TABLE 1

| | | |
|---|---|---|
| Structural formula | (structure with $CF_3$) | (structure with $C_2F_5$) |
| Name | (Trifluoromethyl-cyclohexadiene)tricarbonylruthenium | (Pentafluoroethyl-cyclohexadiene)tricarbonylruthenium |
| Structural formula | (structure with $F_3C$, $CF_3$) | (structure with $F_5C_2$, $CF_3$) |
| Name | (Bistrifluoromethyl-cyclohexadiene)tricarbonylruthenium | (Pentafluoroethyl-trifluoromethyl-cyclohexadiene)tricarbonylruthenium |
| Structural formula | (structure with $CF_3$) | (structure with $C_2F_5$) |
| Name | (Trifluoromethylbutadiene)tricarbonylruthenium | (Pentafluoroethylbutadiene)tricarbonylruthenium |
| Structural formula | (structure with $F_5C_2$, $CF_3$) | (structure with $F_3C$, $CF_3$) |
| Name | (Pentafluoroethyl-trifluoromethylbutadiene)tricarbonylruthenium | (Bistrifluoromethylbutadiene)tricarbonylruthenium |

TABLE 1-continued

| Structural formula | (Trifluoromethyl-cyclooctatetraene)tricarbonylruthenium | (Pentafluoroethyl-cyclooctatetraene)tricarbonylruthenium |
|---|---|---|
| Name | (Trifluoromethyl-cyclooctatetraene)tricarbonylruthenium | (Pentafluoroethyl-cyclooctatetraene)tricarbonylruthenium |

Secondly, the method for producing the ruthenium complex that constitutes the raw material for chemical deposition according to the present invention will be described. This ruthenium complex can be synthesized by reacting dodecacarbonyltriruthenium (hereinafter referred to as DCR) and a polyene derivative that has been partially substituted with fluoroalkyl group(s). As mentioned above, since the bonding force between the DCR and polyene derivative is strong in the ruthenium complex of the present invention, the synthesis method therefor progresses relatively easily. Furthermore, at this time, the use amount of the polyene derivative to be reacted with the DCR can be decreased. Specifically, the necessary reaction amount of the polyene derivative with respect to DCR is a 1 to 3-fold equivalent amount (molar ratio). With regard to this point, in the production of the above-mentioned conventional ruthenium complexes (Chemical Formulas 1 and 2), the polyene cannot be coordinated unless excess polyene (cyclooctatetraene, cyclohexadiene), which is in an amount of 6 to 7-fold equivalent amount with respect to DCR, is used. Considering this point, the ruthenium complex in the present invention can be produced by the use of the polyene (derivative) in a smaller amount than conventional amounts, and this can contribute to the decrease of the production cost thereof.

Furthermore, the reaction for synthesizing the ruthenium complex in the present invention can be progressed by only a thermal reaction, and thus does not require the assist of irradiation of light. Specifically, the ruthenium complex in the present invention can be synthesized by only heating the reaction system so as to become 75 to 85° C. This point also contributes to the decrease of the production cost of the complex.

The step for producing the ruthenium complex of the present invention specifically includes dissolving DCR and a polyene derivative in a suitable solvent (for example, hexane or the like), and heating (refluxing) the solvent. The solvent and the unreacted polyene derivative are distilled off from the reaction liquid, and the ruthenium complex can be collected by solvent extraction. The obtained ruthenium complex can be formed into a raw material for chemical deposition by suitable purification.

The method for forming a thin film by the raw material for chemical deposition according to the present invention conforms to a general chemical deposition method. Specifically, a raw material for chemical deposition formed of a ruthenium complex is vaporized to form a reaction gas, this reaction gas is introduced onto a surface of a substrate, and the ruthenium complex on the surface of the substrate is decomposed to precipitate ruthenium. At this time, the ruthenium complex as a raw material can be vaporized by an arbitrary method. Specifically, since the ruthenium complex of the present invention can be formed into a liquid at an ordinary temperature, a system for bubbling the raw material in the raw material container can also be adopted. In addition, thermal vaporization by a vaporizer may also be conducted depending on the use environment.

The temperature for heating the substrate is preferably within the range from 200° C. to 400° C. Since the decomposition temperature of the ruthenium complex of the present invention is a moderately low temperature, a film can be formed within this temperature range. Furthermore, it is preferable that the atmosphere in the reactor is a reduced pressure atmosphere at from 5 to 10,000 Pa.

Advantageous Effect of Invention

As explained above, the ruthenium complex that is applied in the present invention has suitable stability and decomposition temperature, and also has a high vapor pressure. Furthermore, the producing method therefor is also optimized, and thus the production is possible at a relatively low cost. The raw material for chemical deposition according to the present invention can be preferably used in chemical deposition such as a CVD process and an ALD process.

DESCRIPTION OF EMBODIMENTS

First Embodiment

In this embodiment, (trifluoromethyl-cyclohexadiene)tricarbonylruthenium having carbonyl groups and a trifluoromethyl derivative of cyclohexadiene as ligands (the following formula) was produced.

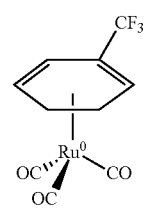

[Chemical Formula 4]

50.5 g of DCR was dissolved in 1.0 L of hexane as a solvent in a three-necked flask, and 70 g of trifluoromethyl-cyclohexadiene was further dissolved. The trifluoromethyl-cyclohexadiene at this time is in a twice equivalent amount (molar ratio) with respect to the DCR. This reaction liquid was then refluxed at 85° C. for 20 hours. After the reflux, the reaction liquid was distilled off under a reduced pressure, and purification was conducted by a silica gel column containing hexane as a developing solvent to collect (trifluoromethyl-cyclohexadiene)tricarbonylruthenium.

The yield amount of the (trifluoromethyl-cyclohexadiene)tricarbonylruthenium obtained by the above-mentioned step was 66.3 g, and the yield thereof was 84%. As mentioned above, trifluoromethyl-cyclohexadiene in a twice equivalent amount with respect to DCR was used in this embodiment, and only a thermal reaction was conducted. Accordingly, (trifluoromethyl-cyclohexadiene)tricarbonylruthenium can be produced at a sufficient yield even under a condition in which no photoreaction is used and the reaction amount of the polyene is suppressed.

Secondly, the physical properties of the produced (trifluoromethyl-cyclohexadiene)tricarbonylruthenium were evaluated. Firstly, an analysis by TG-DTA was conducted. The analysis conditions were a heating temperature range in the air: room temperature to 500° C., and a temperature raising velocity: 5° C./min. In this analysis, (cyclohexadiene)tricarbonylruthenium (Chemical Formula 2), which is a conventional ruthenium complex, was similarly analyzed for the purpose of comparison.

Figure 1:
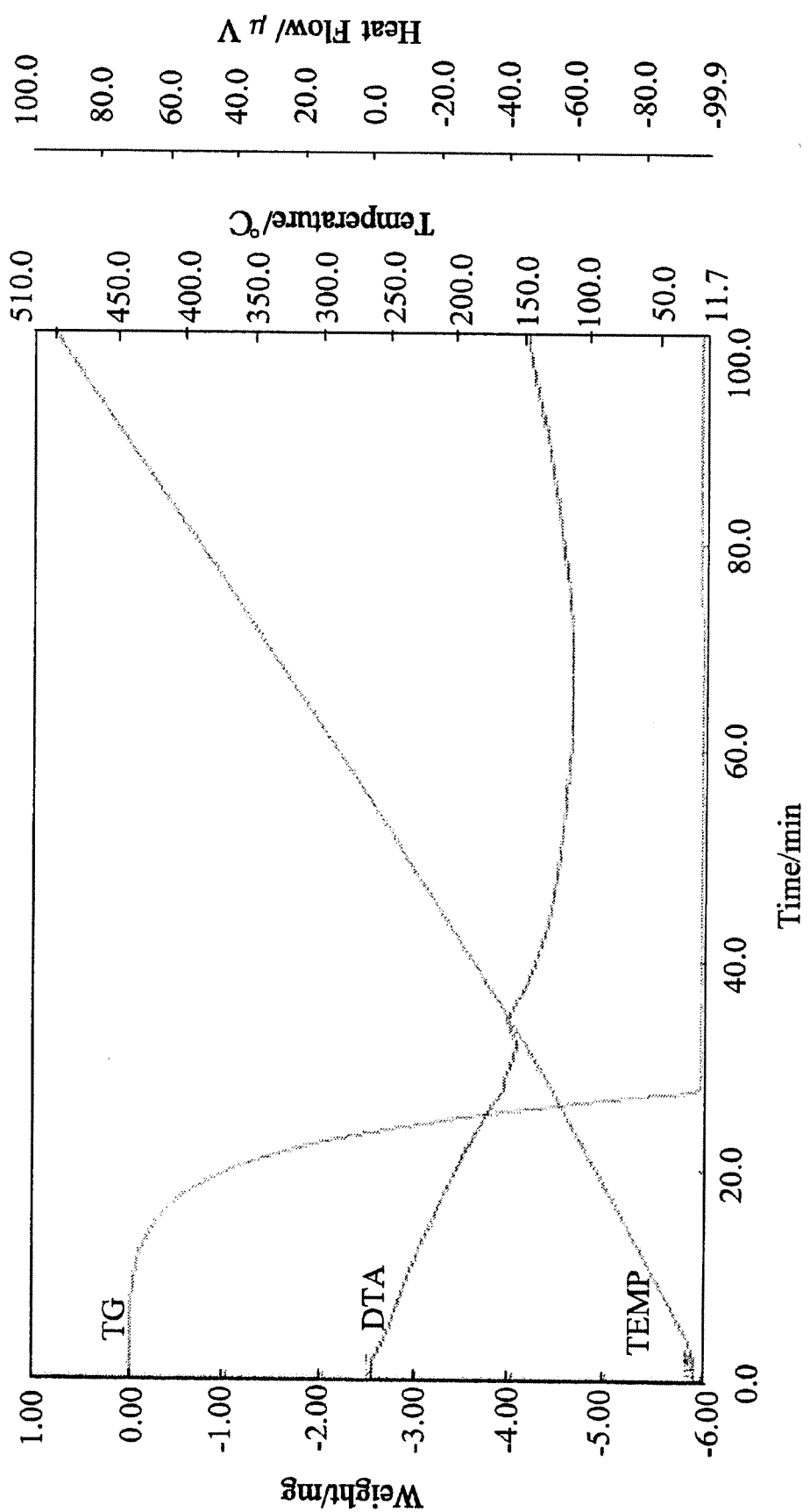
FIG. 1 is a TG-DTA curve of (trifluoromethyl-cyclohexadiene)tricarbonylruthenium produced in this embodiment.
Figure 2:
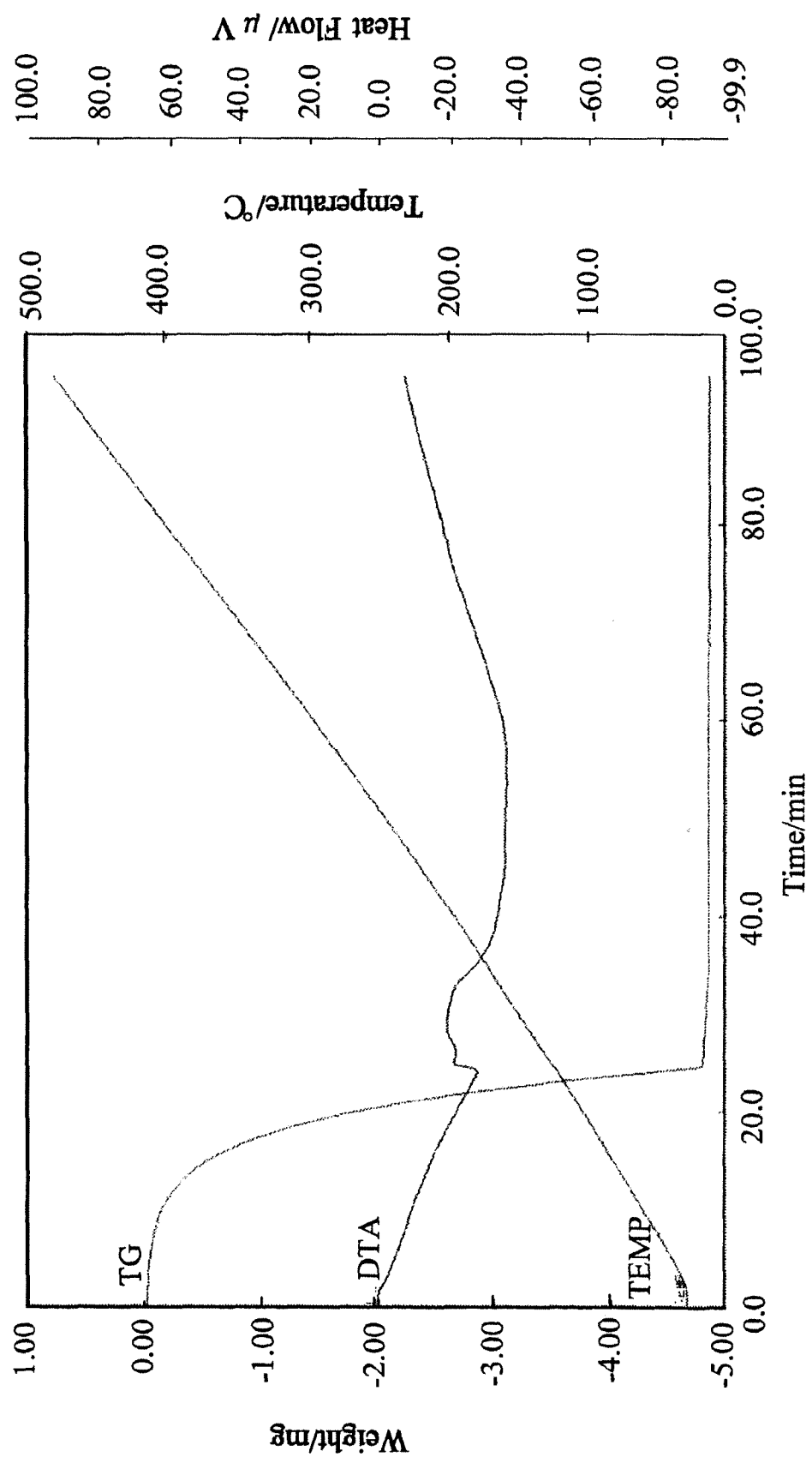
FIG. 2 is a TG-DTA curve of (cyclohexadiene)tricarbonylruthenium as a conventional art.

FIG. 1 is a TG-DTA curve of the (trifluoromethyl-cyclohexadiene)tricarbonylruthenium in this embodiment. FIG. 2 is a TG-DTA curve of (cyclohexadiene)tricarbonylruthenium as a comparative example. From these analysis results, firstly, when the temperature at which the evaporation of the ruthenium complex initiated and the temperature at which the evaporation was completed are seen, the (trifluoromethyl-cyclohexadiene)tricarbonylruthenium in this embodiment began to evaporate at around 90° C., and the evaporation was completed at around 140° C. On the other hand, the (cyclohexadiene)tricarbonylruthenium began to evaporate at around 80° C., and the evaporation was completed at around 130° C. When the evaporation temperatures are considered, these evaporation temperatures are not different significantly, and the temperature of the (cyclohexadiene)tricarbonylruthenium is slightly lower than that of the other. However, when the DTA curve of the (cyclohexadiene)tricarbonylruthenium is seen, the generation and disappearance of the exothermic peak are seen at the temperature around or more than the temperature at which the evaporation was completed. The reason therefor is considered that the (cyclohexadiene)tricarbonylruthenium did not evaporate completely and formed a partially decomposed product, and the product was combusted and evaporated. Specifically, in the case of (cyclohexadiene)tricarbonylruthenium, this may be decomposed even in an evaporation temperature range, and this indicates that the ruthenium complex is partially decomposed depending on the setting of the vaporization temperature of the raw material in the case when the ruthenium complex is used as a raw material for chemical deposition. This makes the presetting of the film formation conditions severe. On the other hand, it is understood that no decomposition product was generated at the completion of the evaporation in the (trifluoromethyl-cyclohexadiene)tricarbonylruthenium of this embodiment, and thus the evaporation was stably conducted.

Secondly, the results of the measurements of the vapor pressure and melting point of the (trifluoromethyl-cyclohexadiene)tricarbonylruthenium are shown in the following table.

TABLE 2

| | Melting point | Vapor pressure | Decomposition temperature |
|---|---|---|---|
| The present embodiment (Ru(CF$_3$CHD) (CO)$_3$) | <−20° C. | 2.25 Torr (at 50° C.) | >140° C. |
| Comparative Example (Ru(CHD) (CO)$_3$) | 20° C. | 0.3 Torr (at 55° C.) | ≈120° C. |

* The decomposition temperatures are described as values expected from the above-mentioned TG-DTA From the table, the (trifluoromethyl-cyclohexadiene)tricarbonylruthenium of this embodiment can maintain a liquid state at from the melting point thereof to an ordinary temperature. Furthermore, the vapor pressure is sufficiently high. The (cyclohexadiene)tricarbonylruthenium, which is a conventional art, has a higher melting point and a lower vapor pressure than those of this embodiment. This is considered to be due to that the substituents were introduced in the cyclohexadiene and fluoroalkyl groups were selected as the substituents.

Secondly, using the (trifluoromethyl-cyclohexadiene)tricarbonylruthenium of this embodiment as a raw material for chemical deposition, a test for film formation of a ruthenium thin film was conducted. As a film formation apparatus, a cold wall type CVD apparatus in which only a substrate stage in a chamber is heated was used. A carrier gas for transferring a vapor of the raw material compound onto a substrate is controlled to be a predetermined flow amount by a mass flow controller. As the substrate for forming a ruthenium thin film, a Si wafer on which a SiO$_2$ coating had been formed in advance by thermal oxidation was used. The other film formation conditions are as follows.

Figure 3:
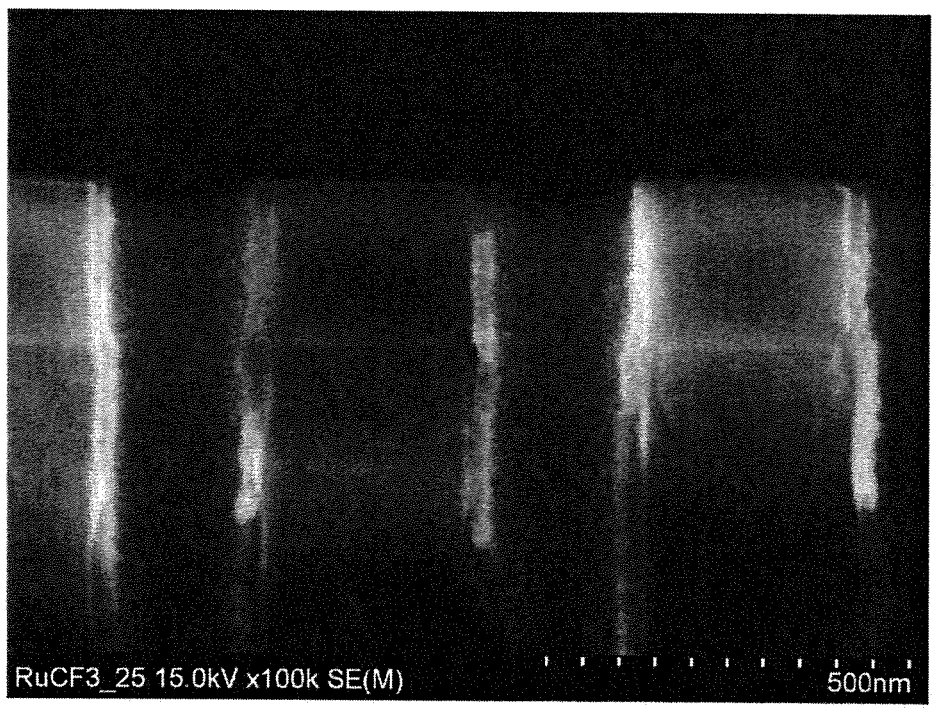
FIG. 3 is a SEM photograph of the ruthenium thin film produced from the (trifluoromethyl-cyclohexadiene)tricarbonylruthenium produced in this embodiment.
Figure 3:
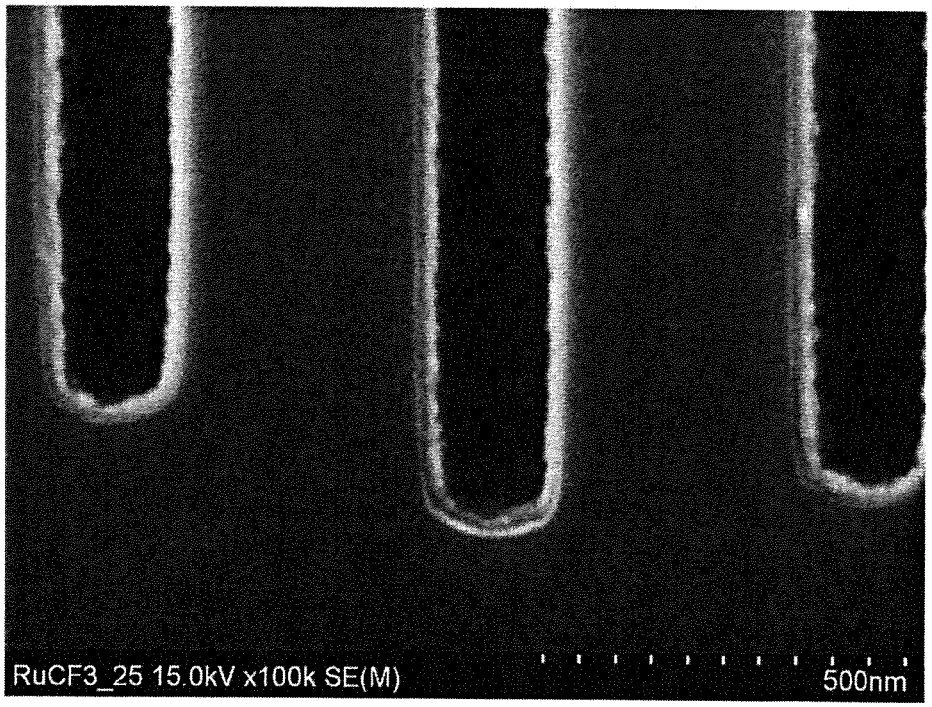

Raw material heating temperature: 70° C.
Substrate heating temperature: 175° C.
Carrier gas (argon) flow amount: 10 sccm
Reaction gas (oxygen) flow amount: 2 sccm
Reaction chamber pressure: 50 Pa
Film formation time: 20 minutes When the film formation test was conducted under the above-mentioned conditions, a ruthenium film having metallic gloss was formed. The SEM photograph for this substrate is shown in FIG. 3, and homogeneous thin films were formed on the upper parts and lower parts of the pores. It was confirmed from this result that a raw material for chemical deposition formed of (trifluoromethyl-cyclohexadiene)tricarbonylruthenium is useful for the formation of a high quality thin film.

Second Embodiment

In this embodiment, (pentafluoroethyl-cyclohexadiene) tricarbonylruthenium having carbonyl groups and a pentafluoroethyl derivative of cyclohexadiene as ligands (the following formula) was produced.

[Chemical Formula 5]

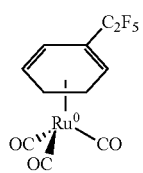

50.5 g of DCR was dissolved in 1.0 L of hexane as a solvent in a three-necked flask, and 93.9 g of pentafluoroethyl-cyclohexadiene was dissolved. The pentafluoroethyl-cyclohexadiene at this time is in a twice equivalent amount (molar ratio) with respect to the DCR. This reaction liquid was then refluxed at 85° C. for 20 hours. After the reflux, the reaction liquid was distilled off under a reduced pressure, and purification was conducted by a silica gel column containing hexane as a developing solvent to collect (pentafluoroethyl-cyclohexadiene)tricarbonylruthenium.

The yield amount of the (pentafluoroethyl-cyclohexadiene)tricarbonylruthenium obtained by the above-mentioned step was 76.3 g, the yield thereof was 84%, and the melting point was −20° C. or less.

Third Embodiment

In this embodiment, (bistrifluoromethyl-cyclohexadiene)tricarbonylruthenium having carbonyl groups and a trifluoromethyl derivative of cyclohexadiene as ligands (the following formula) was produced.

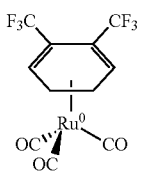

[Chemical Formula 6]

50.5 g of DCR was dissolved in 1.0 L of hexane as a solvent in a three-necked flask, and 102.4 g of bistrifluoromethyl-cyclohexadiene was further dissolved. The bistrifluoromethyl-cyclohexadiene at this time is in a twice equivalent amount (molar ratio) with respect to the DCR. This reaction liquid was then refluxed at 85° C. for 20 hours. After the reflux, the reaction liquid was distilled off under a reduced pressure, and purification was conducted by a silica gel column containing hexane as a developing solvent to collect (bistrifluoromethyl-cyclohexadiene)tricarbonylruthenium.

The yield amount of the (bistrifluoromethyl-cyclohexadiene)tricarbonylruthenium obtained by the above-mentioned step was 77.0 g, the yield thereof was 81%, and the melting point was −20° C. or less.

Fourth Embodiment

In this embodiment, (pentafluoroethyltrifluoromethyl-butadiene)tricarbonylruthenium having carbonyl groups and a trifluoromethyl derivative of butadiene as ligands (the following formula) was produced.

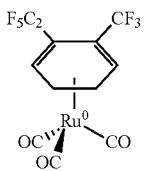

[Chemical Formula 7]

50.5 g of DCR was dissolved in 1.0 L of hexane as a solvent in a three-necked flask, and 125.8 g of pentafluoroethyltrifluoromethylcyclohexadiene was dissolved. The pentafluoroethyltrifluoromethyl-butadiene at this time is in a twice equivalent amount (molar ratio) with respect to the DCR. This reaction liquid was then refluxed at 80° C. for 20 hours. After the reflux, the reaction liquid was distilled off under a reduced pressure, and purification was conducted by a silica gel column containing hexane as a developing solvent to collect (pentafluoroethyltrifluoromethylcyclohexadiene)tricarbonylruthenium.

The yield amount of the (pentafluoroethyltrifluoromethylcyclohexadiene)tricarbonylruthenium obtained by the above-mentioned step was 84.5 g, the yield thereof was 79%, and the melting point was −20° C. or less.

Fifth Embodiment

In this embodiment, (pentafluoroethyl-butadiene)tricarbonylruthenium having carbonyl groups and a trifluoromethyl derivative of butadiene as ligands (the following formula) was produced.

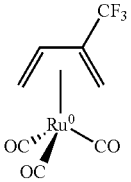

[Chemical Formula 8]

50.5 g of DCR was dissolved in 1.0 L of hexane as a solvent in a three-necked flask, and 57.9 g of trifluoromethyl-butadiene was further dissolved. The trifluoromethyl-butadiene at this time is in a twice equivalent amount (molar ratio) with respect to the DCR. This reaction liquid was then refluxed at 80° C. for 20 hours. After the reflux, the reaction liquid was distilled off under a reduced pressure, and purification was conducted by a silica gel column containing hexane as a developing solvent to collect (trifluoromethyl-butadiene)tricarbonylruthenium.

The yield amount of the (trifluoromethyl-butadiene)tricarbonylruthenium obtained by the above-mentioned step was 59.7 g, the yield thereof was 82%, and the melting point was −20° C. or less.

Sixth Embodiment

In this embodiment, (pentafluoroethyl-butadiene)tricarbonylruthenium having carbonyl groups and a pentafluoroethyl derivative of butadiene as ligands (the following formula) was produced.

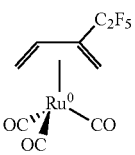

[Chemical Formula 9]

50.5 g of DCR was dissolved in 1.0 L of hexane as a solvent in a three-necked flask, and 81.6 g of pentafluoroethyl-butadiene was further dissolved. The pentafluoroethyl-butadiene at this time is in a twice equivalent amount (molar ratio) with respect to the DCR. This reaction liquid was then refluxed at 80° C. for 20 hours. After the reflux, the reaction liquid was distilled off under a reduced pressure, and purification was conducted by a silica gel column containing hexane as a developing solvent to collect (pentafluoroethyl-butadiene)tricarbonylruthenium.

The yield amount of the (pentafluoroethyl-butadiene)tricarbonylruthenium obtained by the above-mentioned step was 66.9 g, the yield thereof was 79%, and the melting point was −20° C. or less.

Seventh Embodiment

In this embodiment, (pentafluoroethyltrifluoromethyl-butadiene)tricarbonylruthenium having carbonyl groups and a pentafluoroethyltrifluoromethyl derivative of butadiene as ligands (the following formula) was produced.

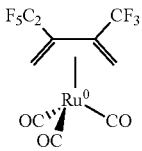

[Chemical Formula 10]

50.5 g of DCR was dissolved in 1.0 L of hexane as a solvent in a three-necked flask, and 113.5 g of pentafluoroethyltrifluoromethyl-butadiene was further dissolved. The pentafluoroethyltrifluoromethyl-butadiene at this time is in a twice equivalent amount (molar ratio) with respect to the DCR. This reaction liquid was then refluxed at 80° C. for 20 hours. After the reflux, the reaction liquid was distilled off under a reduced pressure, and purification was conducted by a silica gel column containing hexane as a developing solvent to collect (pentafluoroethyltrifluoromethyl-butadiene)tricarbonylruthenium.

The yield amount of the (pentafluoroethyltrifluoromethyl-butadiene)tricarbonylruthenium obtained by the above-mentioned step was 79.6 g, the yield thereof was 79%, and the melting point was −20° C. or less.

Eighth Embodiment

In this embodiment, (bistrifluoromethyl-butadiene)tricarbonylruthenium having carbonyl groups and a trifluoromethyl derivative of butadiene as ligands (the following formula) was produced.

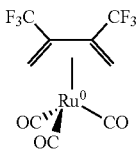

[Chemical Formula 11]

50.5 g of DCR was dissolved in 1.0 L of hexane as a solvent in a three-necked flask, and 90.1 g of bistrifluoromethyl-butadiene was further dissolved. The bistrifluoromethyl-butadiene at this time is in a twice equivalent amount (molar ratio) with respect to the DCR. This reaction liquid was then refluxed at 80° C. for 20 hours. After the reflux, the reaction liquid was distilled off under a reduced pressure, and purification was conducted by a silica gel column containing hexane as a developing solvent to collect (bistrifluoromethyl-butadiene)tricarbonylruthenium.

The yield amount of the (bistrifluoromethyl-butadiene)tricarbonylruthenium obtained by the above-mentioned step was 72.9 g, the yield thereof was 82%, and the melting point was −20° C. or less.

Ninth Embodiment

In this embodiment, (trifluoromethyl-cyclooctatetraene)tricarbonylruthenium having carbonyl groups and a trifluoromethyl derivative of cyclooctatetraene as ligands (the following formula) was produced.

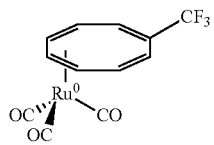

[Chemical Formula 12]

50.5 g of DCR was dissolved in 1.0 L of hexane as a solvent in a three-necked flask, and 102.1 g of trifluoromethyl-cyclooctatetraene was further dissolved. The trifluoromethyl-cyclooctatetraene at this time is in a 2.5-fold equivalent amount (molar ratio) with respect to the DCR. This reaction liquid was then refluxed at 85° C. for 48 hours. After the reflux, the reaction liquid was distilled off under a reduced pressure, and purification was conducted by an alumina column containing hexane as a developing solvent to collect (trifluoromethyl-cyclooctatetraene)tricarbonylruthenium.

The yield amount of the (trifluoromethyl-cyclooctatetraene)tricarbonylruthenium obtained by the above-mentioned step was 64.4 g, the yield thereof was 76%, and the melting point was −20° C. or less.

Tenth Embodiment

In this embodiment, (pentafluoroethyl-cyclooctatetraene)tricarbonylruthenium having carbonyl groups and a pentafluoroethyl derivative of cyclooctatetraene as ligands (the following formula) was produced.

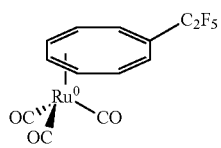

[Chemical Formula 13]

50.5 g of DCR was dissolved in 1.0 L of hexane as a solvent in a three-necked flask, and 142.4 g of pentafluoroethyl-cyclooctatetraene was further dissolved. The pentafluoroethyl-cyclooctatetraene at this time is in a 2.5-fold equivalent amount (molar ratio) with respect to the DCR. This reaction liquid was then refluxed at 85° C. for 48 hours. After the reflux, the reaction liquid was distilled off under a reduced pressure, and purification was conducted by an alumina column containing hexane as a developing solvent to collect (pentafluoroethyl-cyclooctatetraene)tricarbonylruthenium.

The yield amount of the (pentafluoroethyl-cyclooctatetraene)tricarbonylruthenium obtained by the above-mentioned step was 80.6 g, the yield thereof was 80%, and the melting point was −20° C. or less.

Each of the ruthenium complexes produced in the above-mentioned second to tenth embodiments was able to be produced by a polyene derivative in a twice equivalent amount with respect to the DCR, and was able to be synthesized by only a thermal reaction. Furthermore, either of the ruthenium complexes had a sufficient yield. Since these ruthenium complexes have a low melting point and maintain a liquid state at an ordinary temperature, they are preferable as raw materials for chemical deposition.

INDUSTRIAL APPLICABILITY

Since the ruthenium complex that constitutes the raw material for chemical deposition according to the present invention has a high vapor pressure and a moderate decomposition temperature, a high-precision ruthenium/ruthenium compound platinum thin film can be formed at a low temperature. The raw material for chemical deposition according to the present invention can be produced at a relatively low cost, and thus can also contribute to the decrease in cost for the formation of a thin film.

The invention claimed is:

1. A raw material for producing a ruthenium thin film or a ruthenium compound thin film by a chemical deposition method, and comprising a ruthenium complex,
    wherein the ruthenium complex is represented by the following formula, in which carbonyl groups and a fluoroalkyl derivative of a polyene are coordinated to ruthenium:

$(n\text{R-L})\text{Ru}(\text{CO})_3$ wherein L is a polyene having a carbon number of from 4 to 8 and 2 to 4 double bonds, wherein the polyene L has n (n≥1) pieces of substituents R, wherein the substituents Rs are each a fluoroalkyl group having a carbon number of from 1 to 6 and a fluorine number of from 1 to 13, and in the case when the polyene L has two or more (n≥2) of the substituents Rs, the carbon numbers and the fluorine numbers of the substituents Rs may be different in the same molecule.

2. The raw material for chemical deposition according to claim 1, wherein the polyene (L) is a chain polyene or cyclic polyene having a carbon number of from 4 to 6 and having two double bonds.

3. The raw material for chemical deposition according to claim 1, wherein the fluoroalkyl groups (R) as the substituents each has a carbon number of from 1 to 3, a fluorine number of from 1 to 7, and n is 1 to 2.

4. A method for producing the raw material for chemical deposition according to claim 1, which comprises a synthesis step comprising reacting dodecacarbonyltriruthenium and a fluoroalkyl derivative of a polyene under heating,
    wherein the synthesis step is such that the fluoroalkyl derivative of a polyene is reacted in a 1 to 3-fold equivalent amount by molar ratio with respect to the dodecacarbonyltriruthenium.

5. The method for producing the raw material for chemical deposition according to claim 4, wherein the heating temperature in the synthesis step is in the range of 75 to 85° C.

6. A chemical deposition method for a ruthenium thin film or a ruthenium compound thin film, comprising vaporizing a raw material for chemical deposition formed of a ruthenium complex to form a reaction gas, introducing the reaction gas onto a surface of a substrate, and decomposing the ruthenium complex to precipitate ruthenium,
    wherein the raw material for chemical deposition according to claim 1 is used as the raw material for chemical deposition.

7. A method for producing the raw material for chemical deposition according to claim 2, which comprises a synthesis step comprising reacting dodecacarbonyltriruthenium and a fluoroalkyl derivative of a polyene under heating,
    wherein the synthesis step is such that the fluoroalkyl derivative of a polyene is reacted in a 1 to 3-fold equivalent amount by molar ratio with respect to the dodecacarbonyltriruthenium.

8. A method for producing the raw material for chemical deposition according to claim 3, which comprises a synthesis step comprising reacting dodecacarbonyltriruthenium and a fluoroalkyl derivative of a polyene under heating,
    wherein the synthesis step is such that the fluoroalkyl derivative of a polyene is reacted in a 1 to 3-fold equivalent amount by molar ratio with respect to the dodecacarbonyltriruthenium.

9. The method for producing the raw material for chemical deposition according to claim 7, wherein the heating temperature in the synthesis step is in the range of 75 to 85° C.

10. The method for producing the raw material for chemical deposition according to claim 8, wherein the heating temperature in the synthesis step is in the range 75 to 85° C.

11. A chemical deposition method for a ruthenium thin film or a ruthenium compound thin film, comprising vaporizing a raw material for chemical deposition formed of a ruthenium complex to form a reaction gas, introducing the reaction gas onto a surface of a substrate, and decomposing the ruthenium complex to precipitate ruthenium,
    wherein the raw material for chemical deposition according to claim 2 is used as the raw material for chemical deposition.

12. A chemical deposition method for a ruthenium thin film or a ruthenium compound thin film, comprising vaporizing a raw material for chemical deposition formed of a ruthenium complex to form a reaction gas, introducing the reaction gas onto a surface of a substrate, and decomposing the ruthenium complex to precipitate ruthenium,
    wherein the raw material for chemical deposition according to claim 3 is used as the raw material for chemical deposition.

13. The method according to claim 7,
    wherein the fluoroalkyl groups (R) as the substituents each has a carbon number of from 1 to 3, a fluorine number of from 1 to 7, and n is 1 to 2.

14. The method according to claim 13,
    wherein the heating temperature in the synthesis step is in the range of 75 to 85° C.

* * * * *